United States Patent
Baumann et al.

(10) Patent No.: US 6,371,922 B1
(45) Date of Patent: Apr. 16, 2002

(54) METHOD FOR MEASURING BAROREFLEX SENSITIVITY AND THERAPY OPTIMIZATION IN HEART FAILURE PATIENTS

(75) Inventors: Lawrence S. Baumann, Bloomington; Veerichetty A. Kadhiresan, Lino Lakes, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/545,362

(22) Filed: Apr. 7, 2000

(51) Int. Cl.[7] .................................................. A61B 5/00
(52) U.S. Cl. ......................... 600/485; 600/500; 607/17; 607/23
(58) Field of Search .............................. 600/485, 481, 600/500, 505, 526; 607/17, 23

(56) References Cited

U.S. PATENT DOCUMENTS

| | | | |
|---|---|---|---|
| 5,312,452 A | 5/1994 | Salo ............................ | 607/17 |
| 5,334,222 A | 8/1994 | Salo et al. ..................... | 607/17 |
| 5,540,727 A | 7/1996 | Tockman et al. ............. | 607/18 |
| 5,800,471 A | 9/1998 | Baumann ...................... | 607/25 |
| 6,026,324 A | 2/2000 | Carlson ......................... | 607/27 |

OTHER PUBLICATIONS

Bakker, Patricia F., Meijburg H., de Jonge N., et al. Beneficial Effects of Biventricular Pacing in Congestive Heart Failure. (abstract) Pacing Clin Electrophysiol. 1994;17:820.

Cazeau, S., Ritter P., Lazarus A., et al. Multisite Pacing for End–Stage Heart Failure: Early Experience. Pacing Clin Electrophysiol. 1996;19:1748–1757.

Aurricchio A., Salo R. Acute Hemodynamic Improvement by Pacing in Patients with Severe Congestive Heart Failure. Pacing Clin Electrophysiol. 1997;20:313–324.

Blanc JJ., Etienne Y., Gilard M., et al. Evaluation of Different Ventricular Pacing Sites in Patients With Severe Heart Failure: Results of an Acute Hemodynamic Study. Circulation. 1997;96:3273–3277.

Leclercq C., Cazeau S., Le Breton H., et al. Acute Hemodynamic Effects of Biventricular DDD Pacing in Patients With End–Stage Heart Failure. J AM Coll Cardiol 1998;32:1825–1831.

Kass D., Chen CH., Curry C., et al. Improved Left Ventricular Mechanics From Acute VDD Pacing in Patients With Dilated Cardiomyopathy and Ventricular Conduction Delay. Circulation. 1999;99:1567–1573.

(List continued on next page.)

*Primary Examiner*—Robert L. Nasser
(74) *Attorney, Agent, or Firm*—Nikolai & Mersereau, P.A.

(57) ABSTRACT

A method and apparatus for determining the baroreflex sensitivity in a chronic heart failure patient and a method for chronic heart therapy evaluation. The method including providing a series of pacing stimuli to the heart of a chronic heart failure patient and measuring the change in pulse pressure and the change in cycle length incident to each pacing series. The changes being plotted to produce a line indicative of baroreflex sensitivity. The apparatus including a pacemaker having sensors for monitoring both cycle length and pulse pressure wherein the sensors may be integral or separate from the pacemaker. The method for evaluating chronic heart failure therapies including administering a series of therapies and evaluating each therapy based on the resultant increase of the patient's baroreflex sensitivity.

7 Claims, 3 Drawing Sheets

OTHER PUBLICATIONS

Auricchio A., Stellbrink C., Block M., et al. Effect of Pacing Chamber and Atrioventricular Delay on Acute Systolic Function of Paced Patients With Congestive Heart Failure. Circulation. 1999;99:2993–3001.

Aurocchio A., Stellbrink C., Block M., et al. on behalf of the PATH–CHF Study Group. The Pacing Therapies for Congestive Heart Failure (PATH–CHF) Study: Rationale, Design and Endpoints of a Prospective Randomized Multicenter Study. Am J. Cardio. 1999;83:130D–135D.

La Rovere M., Specchia G., Mortara A., et al. Baroreflex Sensitivity, Clinical Correlates and Cardiovascular Mortality Among Patients With a First Myocardial Infarction. A prospective Study. Circulation. 1988;78:816–824.

Mortara A., La Rovere M., Pinna G, et al. Arterial Baroreflex Modulation of Heart Rate in Chronic Heart Failure. Circulation. 1997;96:3450–3458.

Mortara, et al., "Arterial Baroreflex Modulation of Heart Rate in Chronic Heart Failure" pp. 3450–3458 of Circulation vol. 96 #10 from Nov. 18, 1997.

METHOD FOR MEASURING BAROREFLEX SENSITIVITY AND THERAPY OPTIMIZATION IN HEART FAILURE PATIENTS

BACKGROUND OF THE INVENTION

1. Field of the Invention

This invention relates generally to a method and apparatus for assessing baroreflex sensitivity, and particularly to a method and apparatus for establishing an optimum pacing site and AV delay parameter for a programmable pacemaker.

2. Discussion of the Related Art

Congestive heart failure is an insidious disease affecting at least two million Americans. Patients diagnosed with heart failure have an extremely poor long-term prognosis. The average life expectancy of a person suffering from chronic heart failure is now only five years. Because of the severity of chronic heart failure, a need exists for developing efficacious therapies for this disease. The potential market for an efficacious therapy is not only large but also highly motivated. The patient's clinical and hemodynamic status determines the baroreflex sensitivity (BRS) that is a measure of the ability of that individual's heart to react to changes in blood pressure by changing heart rate. The BRS of a chronic heart failure patient parallels that patient's clinical and hemodynamic status. Thus, BRS provides an indicator for the efficacy of a drug therapy or a ventricular resynchronization therapy. BRS may also be used to predict arrhythmic events and mortality in these patients.

Current methods for measuring BRS typically require drug infusion or a Valsalva's maneuver. Drug infusion, typically utilizing phenylephrine, is used to chemically induce vasoconstriction that changes the pulse pressure. The change in pulse pressure induces a change in the heart's cycle length. Both the change in pulse pressure and the change in cycle length are measured relative to established baselines. The two coordinates are plotted on a graph. Repeated administration of the drug develops a regression line having a slope that is a measure of BRS. Similarly, the Valsalva's maneuver mechanically induces a change in pulse pressure to measure BRS to reach the same result as drug infusion. Neither drug infusion nor the Valsalva's maneuver is timely, and the results from measurement using the Valsalva's maneuver are typically less repeatable and hence less reliable than desired for medical applications. Further, drug infusion and the Valsalva's maneuver cause significant patient discomfort and are potentially dangerous to the patient. Therefore, a need exists for a fast, comfortable and reliable method to determine BRS in chronic heart failure patients.

Drug and pacing therapies are commonly used to extend the lives of chronic heart failure patients. With pacing therapies, pacing site and atrioventricular (AV) delay are critical to the efficacy of the therapy. In early pacing devices, the AV delay was not adjustable to fit a patient's changing condition after implantation. Later devices permitted the external reprogramming of the AV delay by the physician, although the parameters evaluated for reprogramming still required the use of invasive techniques to measure.

Other devices utilize heart rate variations associated with changes in the paced AV delay measured over a sufficient time interval that transient (short-term) variations can be ignored and only the steady state variations assessed. Still other devices provide for optimizing both the pacing mode and the AV delay parameter by incorporating a sensor to provide an average value of a physiologic parameter over a predetermined time interval for each change in pacing mode/AV delay interval. The particular AV delay associated with an optimum value for the physiologic parameter is used to establish the optimum AV delay until the algorithm is again executed and a new optimum AV delay is established. Although studies indicate the efficacy of the above therapies, none of the therapies utilize the patient's BRS in determining the appropriate therapy. Given the strong correlation between BRS and a patient's clinical and hemodynamic status, there is need for a method of optimizing therapy based on BRS.

The present invention meets the above needs and provides additional advantages and improvements that will be evident to those skilled in the art.

SUMMARY OF THE INVENTION

The present invention provides an apparatus and method for measuring the BRS of a patient having an implanted pulse generator. In addition the present invention provides a method for determining a therapy's efficacy. The apparatus for measuring baroreflex sensitivity includes a pacemaker, a first sensor and a second sensor. The pacemaker has at least one variable parameter capable of altering a pulse pressure in a patient. The pacemaker may be of the type having atrial and ventricular depolarization sensors, and capable of selectively stimulating the right, the left or both ventricular chambers. The pacemaker typically provides pacing pulses with a selected AV delay following detection of atrial depolarization events. The AV delay may be pre-selected or altered after implantation of the pacemaker. While cycle length is typically described as atrial cycle length, it should be recognized that ventricular cycle length could also be the cycle length used in determining BRS. The pacemaker typically includes a processor receiving data from the first and second sensors and controlling the pulse generator of the pacemaker. The first sensor senses the cycle length of the patient's heart. The second sensor senses the patient's pulse pressure. The first sensor may be selected from the group of electrocardiographic sensors, an atrial electrographic sensors and a ventricular electrographic sensors, among others. The second sensor may be selected from the group of Millar pressure transducers, RV pressure transducers, LV pressure transducers, RV impedance sensors, LV impedance sensors, aortic cuffs, accelerometers, echo catheters, Doppler echo devices, external pressure cuffs, external impedance sensors, radial tonometers, and plethysmogram sensors, among others. The apparatus may include a visual display connected to the pacemaker to display data indicative of the baroreflex sensitivity. The apparatus visual display may be connected to the pacemaker by radio frequency, a wire, or otherwise as is recognized by those skilled in the art. The apparatus may also include an external programmer. The programmer typically has an external processor and a display. The programmer may display data indicative of BRS calculated by the pacemaker's processor or the programmer may include an external processor that receives information from data from the pacemaker's processor and displays data indicative of baroreflex sensitivity on the display. The apparatus may include an implanted transmitter connected to the processor implanted in the patient and a receiver connected to the external processor in the external programmer wherein the implanted transmitter transmits data indicative of baroreflex sensitivity to the receiver. Similarly, the apparatus may include an implanted receiver connected to the processor implanted in the patient and a transmitter connected to the external processor in the external programmer wherein the transmitter transmits data to the receiver to alter the pacing parameters.

The method of measuring BRS in accordance with the present invention uses the pulse generator in the pacemaker to alter the pulse pressure of the patient. This method produces a measurement of BRS analogous to previous methods for BRS measurement and therefore allows for direct comparison. This measurement of pulse pressure also provides an immediate indicator of the efficacy of the particular pacing mode being applied compared with the pulse pressure of the heart's intrinsic rhythm. The method of the present invention, includes the steps of pacing the heart, measuring the changes in pulse pressure and intrinsic cycle length, and calculating the patient's baroreflex sensitivity from these measured parameters. The change in pulse pressure are for purposes of the present invention the difference between a baseline pulse pressure and the actual pulse pressure during pacing. The change in cycle length are for purposes of the present invention the difference between a baseline cycle length and the cycle length induced by the change in pulse pressure. The pacing step includes pacing a heart for a plurality of paced heart beats, wherein each of a pacing series are followed by a plurality of intrinsic heart beats. The plurality of paced beats defined as the pacing series and the plurality of intrinsic heart beats defined as the intrinsic series. The pulse pressure measurement step measures the change in pulse pressure during the pacing series. The pulse pressure may be measured using a method selected from Doppler echo, radial tonometry, thermodilution, dye dilution, MUGA, plethysmography, Fick method, acetylene rebreathing technique and carbon dioxide rebreathing technique. The intrinsic cycle length measurement step measures the change in intrinsic cycle length resulting from the change in pulse pressure during the pacing series. The measurements of these changes may be made during at a quiet time where the patient is at rest. The baroreflex sensitivity is then calculated from the change in pulse pressure measurements and the change in intrinsic cycle length measurements after a plurality of pacing series.

This calculation of baroreflex sensitivity may be used to evaluate the efficacy of therapies and to select the most efficacious therapy that is the therapy producing the highest baroreflex sensitivity. For this application the baroreflex sensitivity is measured before the cardiac rehabilitative therapy. The patient is then provided a cardiac rehabilitative therapy to the CHF patient. The patient's baroreflex sensitivity is again measured after the cardiac rehabilitative therapy. The results of the therapy are then evaluated based on a comparison of the patient's baroreflex sensitivity before the cardiac rehabilitative therapy and the patient's baroreflex sensitivity after the cardiac rehabilitative therapy.

The foregoing features and advantages as well as other features and advantages of the present invention will become apparent to those skilled in the art upon review of the Detailed Description of the Invention, especially when considered in conjunction with the accompanying figures.

DETAILED DESCRIPTION OF THE INVENTION

The present invention is applicable to measurement of baroreflex sensitivity (BRS) and the use of BRS measurement to evaluate therapies. The invention is described in this patent in the context of specific examples and embodiments but the appended claims are not intended to be limited to these specific examples or embodiments.

Figure 1:
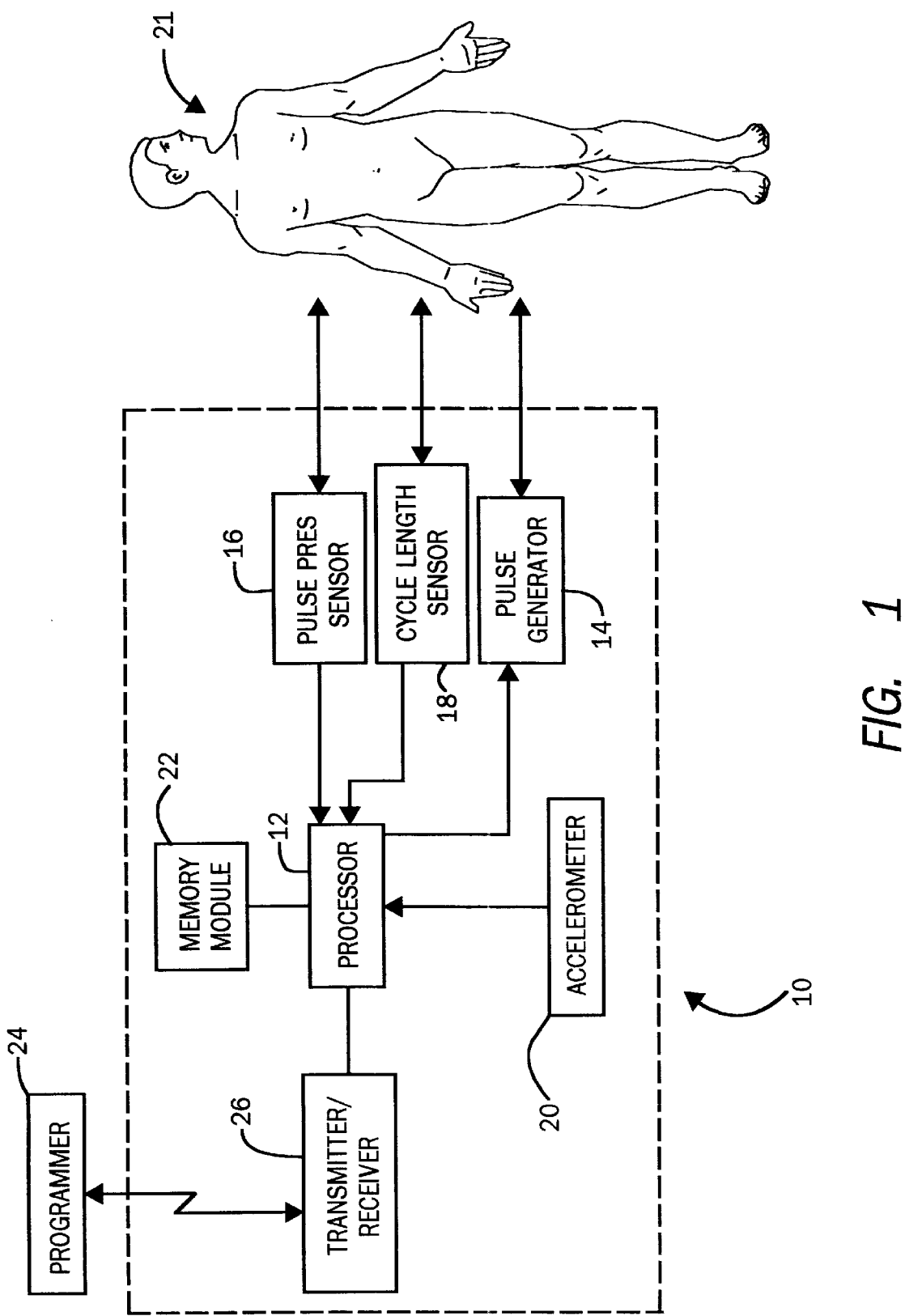
FIG. 1 shows a block diagram of an apparatus for practicing the present invention.

The present invention uses a pacing device to alter the pulse pressure in a patient enabling the measurement of the patient's BRS. FIG. I illustrates an exemplary apparatus 10 configured in accordance with the present invention. Apparatus 10 is generally configured to initiate a transient change in pulse pressure of a patient, to measure the transient change in pulse pressure and to measure the transient intrinsic change in cycle length resulting from the transient change in pulse pressure. Apparatus 10 is typically implanted in the patient. Apparatus 10 includes a processor 12, a pulse generator 14, a pulse pressure sensor 16 and a cycle length sensor 18. Apparatus 10, as shown in FIG. 1, may also include a programmer 24 communicating with processor 12 through a receiver/transmitter 26. Pulse pressure sensor 16 and cycle length sensor 18 may be configured to be external to the patient communicating with programmer 24 through wires or with processor 12 through radio frequencies. Apparatus 10 may also include an accelerometer 20 to determine appropriate periods for measuring a patient's BRS, such as for example a quiet time of reduced activity.

Processor 12 controls pulse generator 14 and receives data from pulse pressure sensor 16 and cycle length sensor 18. Processor 12 communicates with pulse generator 14 to determine the specific parameters of the pacing stimulus to be sent to the patient's heart. The particular parameters used determine the degree that the pulse pressure is altered. Typically, the parameters include AV delay and the site of the pacing stimulus. Pulse generator 14 is typically configured to change the pulse pressure by altering the AV delay and the site of the pacing stimulus, either alone or in combination. To confer a stimulus to the heart, pulse generator 14 is electrically connected to the patient's heart using one or more pacing leads. Processor 12 also communicates with pulse pressure sensor 16. Pulse pressure sensor 16 senses the change in pulse pressure. Pulse pressure sensor 16 may be either implanted in or external to the patient. Typically, pulse pressure sensor 16 is a Millar pressure transducer, an RV pressure transducer, a LV pressure transducer, an RV impedance sensor, a LV impedance sensor, an aortic cuff, an accelerometer, an echo catheter, a Doppler echo device, an external pressure cuff, an external impedance sensor, a radial tonometer, or a plethysmogram sensor. Pulse pressure sensor 16 can utilize a variety of methods to measure blood pressure, including methods that correlate other measured parameters to blood pressure. Processor 12 also communicates with cycle length sensor 18. Cycle length sensor 18 is electrically connected to the patient to sense a signal indicative of cycle length. Cycle length sensor 18 may measure cycle length invasively with an atrial electrogram or from a ventricular electrogram or non-invasively using an electrocardiogram. Cycle length sensor 18 may measure any parameter indicative of cycle length. Cycle length sensor 18 typically includes a plurality of sensors configured to measure the depolarization and repolarization events of a patient's heart to convert them into a suitable waveform indicative of cycle length. These waveforms include but are not limited to any of the features of the PQRST wave from an ECG. For exemplary purposes, a cycle length sensor may include a processor, a first amplifier, a second amplifier, and a lead. The lead is adapted to be coupled to a patient's heart. The lead including a first depolarization sensor and a second depolarization sensor electrically coupled to the first and second amplifiers, respectively. The first depolarization sensor is disposed in the right atrium of the heart and is coupled to the first amplifier by a wire. Similarly, the second depolarization sensor is disposed in the right ventricle and is connected to the second amplifier by a wire. Thus, when the SA node in the right atrium depolarizes, the resulting signal is sensed by the first depolarization sensor, is amplified by the first amplifier and is provided as an input to the processor. A ventricular depolarization signal (R-wave) is likewise sensed by the second depolarization sensor, is amplified by second amplifier and is provided as an input to the processor. The data received from pulse pressure sensor 16 and cycle length sensor 18 may be stored in a memory module 22. The raw data from the sensors or data processed by processor 12 and indicative of the BRS may be stored in memory module 22. Additionally, processor 12 may receive data from accelerometer 20 indicative of the patient's activity level. As mentioned above, accelerometer 20 may also be configured to sense pulse pressure, as disclosed in U.S. Pat. No. 6,026,324 to Carlson, the disclosure of which is hereby incorporated by reference. To communicate data to and from a physician, processor 12 may be connected to an external programmer 24. External programmer 24 may include a display to convey numeric and/or graphical data to the physician or otherwise communicate a patients BRS to the physician. Processor 12 may be connected to programmer 24 directly by wire or indirectly by a transmitter/receiver 26. Transmitter/receiver 26 may transmit signals indicative of data from the sensors and or processor. In an alternative embodiment, programmer 24 includes a processor for receiving raw data from pulse pressure sensor 16 and cycle length sensor 18 and for calculation of a patient's BRS.

Figure 2A:
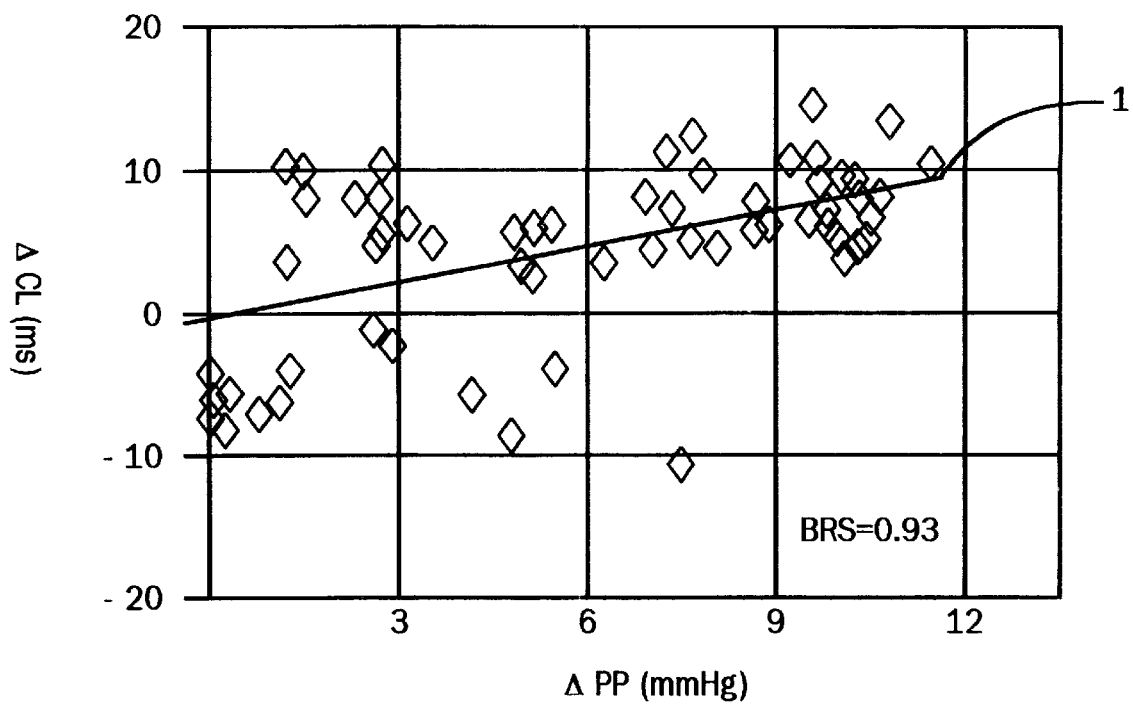
FIG. 2A is a graph showing a line whose slope is indicative of the BRS of a chronic heart failure patient.
Figure 2B:
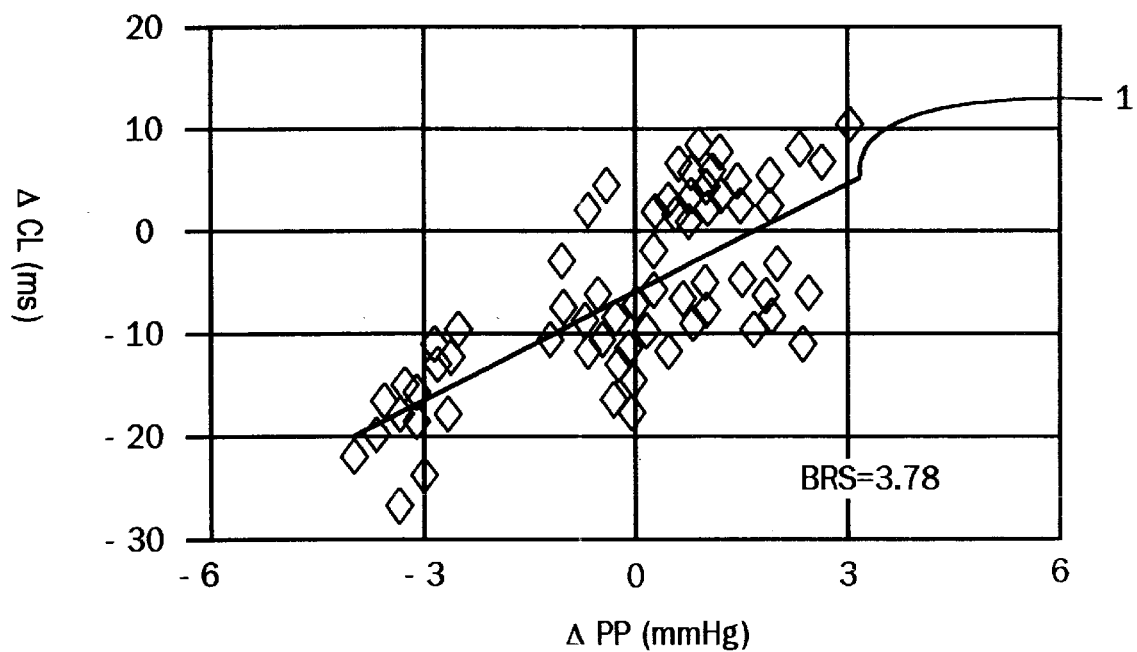
FIG. 2B is a graph showing a line whose slope is indicative of the BRS of a patient having better health than the patient of FIG. 2A.

FIGS. 2A and 2B illustrate graphs of the BRS from two CHF patients using this method. Generally, a larger value of BRS is indicative of a healthier CHF patient. Thus, the BRS value (slope) of 3.78 milliseconds/millimeter of Mercury ((ms)/(mm Hg)), shown in FIG. 2B, represents a patient in better condition than the BRS value (slope) of 0.93 (ms)/(mm Hg), shown in FIG. 2A. To establish a line having a slope representative of BRS, a plurality of points are plotted from the transient change in cycle length versus a transient change in pulse pressure resulting from a pacing stimulus. Different points are established by altering the patient's pulse pressure with the pacemaker. A single line is established from the plurality of points using linear regression. The slope of the regression line is equal to the BRS of the particular patient.

Figure 3:
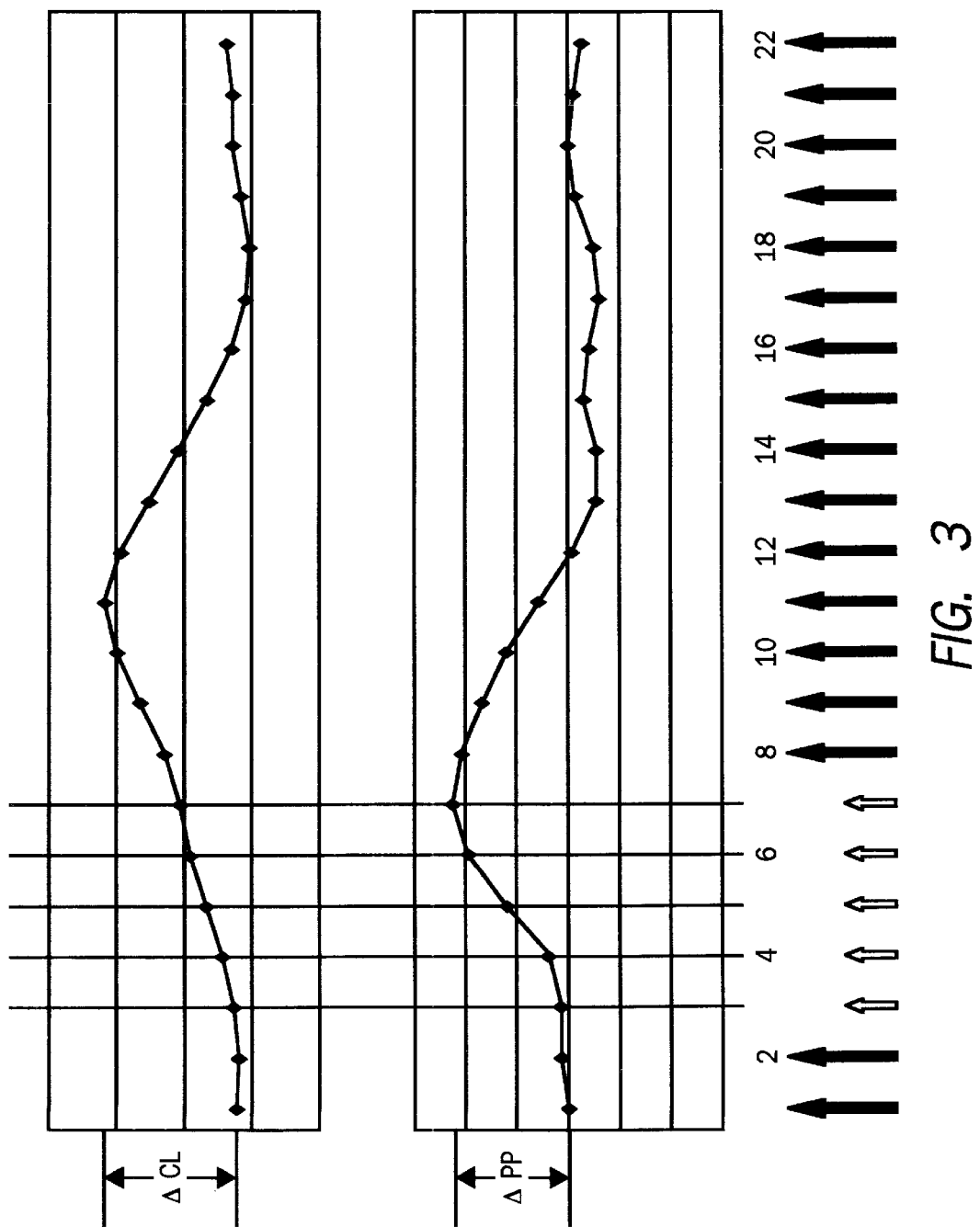
FIG. 3 is a graph of the changes in cycle length and pulse pressure resulting from pacing input that are used in establishing the points for the graph of FIGS. 2A and 2B.

FIG. 3 illustrates the relationship of transient changes in pulse pressure to transient changes in cycle length. Heart beats are represented by arrows and numerically along the X-axis. The solid arrows represent the unpaced intrinsic ventricular beats of the heart and the outlined arrows represent paced ventricular beats controlled by a pacemaker. The values of both the pulse pressure and cycle length are independently represented along the Y-axis. The graph of FIG. 3 shows a steady rise in pulse pressure with each paced ventricular beat, chosen as beats 3 through 7 for exemplary purposes only. This transient increase in pulse pressure relative to a baseline represents a first coordinate along the X-axis ($\Delta PP$). After the paced beats, the heart resumes its intrinsic ventricular rhythm. In response to the transiently increased pulse pressure during beats 3 though 7, the heart intrinsically increases its cycle length in order to reduce the earlier sensed increase in pulse pressure. In the example of FIG. 3, the heart reaches a maximum cycle length at beat 11 before the cycle length decreases. This transient intrinsic increase in cycle length relative to a baseline is the second coordinate along the Y-axis ($\Delta CL$). The cycle length measured in the graphs is atrial cycle length for exemplary purposes only. The cycle length used may be atrial cycle length, ventricular cycle length, or other measures of cycle length that are evident to those skilled in the art. In addition, atrial cycle length can be calculated approximately from a ventricular cycle length measurement:

(time of occurrence of $A$ wave)=((time of occurrence of $V$ wave)–(nominal $AV$ delay))

The first coordinate for $\Delta PP$ and the second coordinate for $\Delta CL$ represent the coordinate pair which is one of the plurality of points used for BRS determination, as shown in FIGS. 2A and 2B.

Referring again to FIG. 3, the pulse pressure is any measure of the patient's blood pressure. For purposes of the present invention, pulse pressure may include any measure indicative of blood pressure, including direct measurements and methods which correlate other measured parameters to blood pressure. Blood pressure, for purposes of the present invention, includes systolic pressure, diastolic pressure, pulse pressure, and mean pressure. Systolic pressure includes maximum systolic pressure and end-systolic pressure. Diastolic pressure includes minimum diastolic pressure and end-diastolic pressure. Pulse pressure includes systolic pressure minus diastolic pressure. The pulse pressure is typically measured with an implanted or an external pressure sensor. As mentioned above, the sensor can utilize a variety of methods to measure blood pressure, including methods that correlate other measured parameters to blood pressure. Invasively, these methods may utilize a Millar pressure transducer, an RV pressure transducer, an LV pressure transducer, an accelerometer, Doppler echo with an echo catheter, RV impedance, LV impedance or an aortic cuff, among others. Non-invasively, these methods may utilize an accelerometer, Doppler echo, a pressure cuff on the arm, external impedance, radial tonometer on the patient's wrist, thermodilution, dye dilution, MUGA (radioisotope), plethysmogram sensor, Fick method, acetylene rebreathing technique, or carbon dioxide rebreathing technique, among others. For purposes of BRS determination, the change in blood pressure from a baseline is the relevant measurement. The measurement of the baseline and the change in pulse pressure are typically taken during a quiet time for the patient. That is, at a time where the cycle length and pulse pressure have stabilized to a resting baseline. This minimizes any variations in pulse pressure resulting from activity of the patient. Techniques for establishing a baseline pressure are known to those skilled in the art. For exemplary purposes, a baseline for the present determination may be established by taking the average pressure from the last 2 to 6 beats before pacing, as shown in FIG. 3. The actual number of beats used to establish a baseline is typically limited by the time available for BRS measurement. It is understood that using a larger number of beats to establish the baseline will result in a more accurate determination. During pacing, the pulse pressure is typically calculated from the average pressure of a subset of the paced beats. Again, the 5 paced beats shown in FIG. 3 are for exemplary purposes only. Typically between 3 and 8 paced beats are used to determine the pressure during pacing. The upper limit is dictated by the time available for measurement and more importantly by the onset of secondary mechanisms, for example vasodilation, that will compensate for increase in pressure. This compensation will alter the change in cycle length necessary for BRS determination and therefore allowing the onset of the secondary mechanisms is typically avoided. The first paced beat is typically omitted because the onset of pacing results in a shortened V—V interval and a small value in pulse pressure. Therefore, for exemplary purposes, a change in pulse pressure may be determined by averaging the pulse pressure from beat number 4 to beat number 7, both of which are paced as shown in FIG. 3, and subtracting the average of the last five beats prior to pacing. Although the pressure during pacing is discussed as an average over a number of beats, the pressure during pacing may be taken from the maximum pressure achieved during pacing or from other methods that will be recognized by those skilled in the art.

As discussed above, the present invention uses a pacemaker to alter the pulse pressure for BRS determination. The magnitude of the pressure change is typically dictated by the pacemaker's AV delay and the site of the pacing stimulus. Other parameters controlled by the pacemaker may also affect the change in pulse pressure. These parameters may include AV delay, the chamber paced, the site within the chamber paced, and the delays between multiple pacing sites, among other parameters. In principle, the baseline need not be non-paced, but could be a particular combination of pacing parameters. When the parameters were changed, the pressure change induced from the original paced baseline could be used to establish BRS. The use of a pacemaker to alter the pulse pressure allows for not only an increase in pulse pressure that increases cycle length but also a decrease in pulse pressure that results in a decrease in cycle length, as shown in FIG. 2B. Some prior methods for BRS measurement, discussed above, did not permit measurement of the heart's response to a pressure decrease. The ability to measure the effects of a decrease in pulse pressure enables a doctor to more comprehensively evaluate a patient's health. For exemplary purposes, the pacemaker may include a pulse generator and a lead adapted to confer a pacing stimulus on the heart. The pulse generator is configured to confer a stimulus at some site on the heart that alters the AV delay or otherwise alters the pulse pressure. When the right ventricle is to be stimulated, the lead is typically attached to the tissue located proximate the apex of the right ventricle. A pulse conferred to the apex of the right ventricle initiates ventricular depolarization that spreads as a wave across both the right and left ventricles. Alternatively, the pulse generator could confer stimulating pulses to stimulate the heart's left ventricle. In addition, if the pacing mode calls for bi-ventricular pacing, the pulse generator may deliver stimulating pulses to both the right and left ventricles. A processor may be provided to control the timing of the impulses. As mentioned above, the impulses from the pulse generator are meant to alter the pulse pressure. To accomplish this, the pulses are typically timed relative to a preceding sensed atrial depolarization signal to redefine an AV delay. As mentioned above, altering the AV delay is one effective method for using a pacemaker to alter the pulse pressure.

The increase in cycle length represented in the graph of FIG. 3 is a result of the pressure increase induced by the pacemaker. The value of cycle length at each beat is typically a smoothed version of the actual value produced from ECG type measurements. The values of the cycle length may be smoothed using least squares, 3-point moving rectangle window, an 11-point moving Blackman window or other techniques known to those skilled in the signal processing art. Again, the measurement used for BRS determination is a change in the cycle length measured from a baseline. The baseline is typically established prior to pacing during a period of rest to avoid any fluctuations due to physical activity. As with pulse pressure, the measurement of the baseline and the change in cycle length are typically taken during a quiet time for the patient. That is, at a time where the cycle length and pulse pressure have stabilized to a resting baseline. This minimizes any variations in cycle length resulting from activity of the patient. Techniques for establishing a baseline cycle length are known to those skilled in the art. For exemplary purposes, a baseline for the present determination may be established by taking the average cycle length from the last 2 to 6 beats before pacing to the second beat after the first paced beat. The actual number of beats used to establish a baseline is typically limited by the time available for BRS measurement. It is understood that using a larger number of beats to establish the baseline will result in a more accurate determination. A cycle length due to pacing is typically calculated from the maximum cycle length when the cycle length due to pacing increases from the baseline cycle length or from the minimum cycle length when the cycle length due to pacing decreases from the baseline cycle length. For exemplary purposes, a baseline cycle length may be determined from the average of five beats in FIG. 3: from beat number 1 to beat number 5. The cycle length due to pacing may be determined from 6 beats in FIG. 3: from beat number 5 to beat number 10. If the magnitude of ((the maximum cycle length among the 6 beats) minus (the baseline cycle length)) is greater than the magnitude of ((the minimum cycle length among the 6 beats) minus (the baseline cycle length)), then the change in cycle length is the maximum cycle length among the 6 beats minus the baseline cycle length. Otherwise, the change in cycle length is the minimum cycle length among the 6 beats minus the baseline cycle length.

In application and use, the method and apparatus of the present invention initiate a plurality of pacing algorithms to provide a sufficient number of data points to develop a line on a $\Delta$CL versus $\Delta$PP graph, as shown in FIG. 2. In theory, the line can be established with only two points. In practice, typically about 75 points are established and a line is developed using linear regression. The slope of this line in units of (ms)/(mm Hg) is the BRS. To achieve a sufficient number of points, the pacemaker initiates a variety of pacing modes wherein variation in AV delay, pacing site and other pacing parameters, either alone or in combination, are altered to alter pulse pressure. These modes may be programmed into a pacemaker or may be initiated externally from an external controller, either running a particular predetermined program or manually determined by an operator. To avoid the influence that the order of the modes' application, their order of application is typically randomized. Once a sufficient number of points have been generated, linear regression is used to establish the line for BRS determination.

The above described method and apparatus can be used to evaluate the efficacy of therapies for CHF patients. To evaluate a therapy, a particular therapy is administered to a CHF patient for a therapy period. The therapy period is long enough to demonstrate the therapy's effectiveness in treating CHF. Immediately after the therapy period, the BRS is measured using the above-described techniques. The BRS is recorded. Following the therapy, there is a washout period where no therapy is administered. The washout period is long enough to allow the heart to resume its original condition before the therapy. A second therapy is then administered to the CHF patient for the same period as the prior therapy. Immediately after the second therapy period, the BRS is again measured using the above identified techniques and recorded. A second washout period follows. The above-cycle of therapy period, BRS measurement and washout period continues until all of the potential therapies have been evaluated. The therapy period providing the greatest increase in the BRS is deemed to be the most efficacious of the evaluated therapies. The optimal therapy, drug, pacing or combination thereof, is applied to the particular patient. An additional step of measuring the BRS after the washout cycle may be provided to assure the baseline BRS is similar to the pre-therapy BRS.

Both the calculation of BRS and the evaluation of CHF therapies may be programmed for automatic execution into a programmable pacemaker having a cycle length sensor and a pressure sensor. In the case of automated calculations and evaluations, the pacemaker may additionally be provided with an accelerometer to measure the activity level of the patient. The accelerometer assures more accurate determinations by allowing the determinations to be made only at quiet times.

This invention has been described herein in considerable detail in order to provide those skilled in the art with the information needed to apply the novel principles and to construct and use such specialized components as are required. However, as discussed above, it is to be understood that the invention can be carried out by specifically different equipment and devices, and that numerous modifications, both as to the equipment and operating procedures, can be accomplished without departing from the scope of the invention itself.

What is claimed is:

1. A method for measuring baroreflex sensitivity and adjusting patient therapy based on measured values, comprising:

pacing a heart for a plurality of paced heart beats, wherein the plurality of paced beats comprise a pacing series and each of the pacing series is followed by a plurality of intrinsic heart beats, wherein the plurality of intrinsic heart beats comprise an intrinsic series measuring a change in pulse pressure during the pacing series;

measuring a change in intrinsic cycle length resulting from the change in pulse pressure during the pacing series;

calculating baroreflex sensitivity from the change in pulse pressure measurements and the change in intrinsic cycle length measurements after a plurality of pacing series, and adjusting a therapy to maximize the calculated baroreflex sensitivity.

2. A method, as in claim 1, wherein adjusting patient therapy comprises changing at least one of AV delay, right ventricle stimulation, left ventricle stimulation, and atrial sensing of a pacemaker implanted in the patient.

3. A method, as in claim 1, wherein measuring the change in pulse pressure includes determining an intrinsic pulse pressure at the patient's quiet time.

4. A method, as in claim 3, wherein measuring a change in pulse pressure includes using a sensor selected from the group consisting of a Millar pressure transducer, an RV pressure transducer, a LV pressure transducer, an RV impedance sensor, a LV impedance sensor, an aortic cuff, an accelerometer, an echo catheter, a Doppler echo device, an external pressure cuff, an external impedance sensor, a radial tonometer, and a plethysmogram sensor.

5. A method, as in claim 3, wherein measuring a change in pulse pressure includes using a method selected from the group consisting of Doppler echo, radial tonometry, thermodilution, dye dilution, MUGA, plethysmography, Fick method, acetylene rebreathing technique and carbon dioxide rebreathing technique.

6. A method, as in claim 1, wherein the step of measuring a change in intrinsic cycle length includes using one of an electrocardiographic sensor, an atrial electrographic sensor and a ventricular electrographic sensor.

7. A method for measuring baroreflex sensitivity and adjusting patient therapy based on measured values, comprising:

a step for pacing a heart for a plurality of paced heart beats, wherein the plurality of paced beats comprise a pacing series and each of the pacing series are followed by a plurality of intrinsic heart beats, wherein the plurality of intrinsic heart beats comprise an intrinsic series;

a step for determining a change in pulse pressure during the pacing series;

a step for determining a change in intrinsic cycle length resulting from the change in pulse pressure;

a step for determining baroreflex sensitivity based on the change of cycle length divided by the change in pulse pressure, and a step for selecting a therapy that optimizes the determined baroreflex sensitivity.

* * * * *